United States Patent
Van Alstine et al.

(10) Patent No.: US 9,797,871 B2
(45) Date of Patent: Oct. 24, 2017

(54) METHOD FOR STORAGE AND STABILIZATION OF A TARGET SUBSTANCE

(75) Inventors: James Van Alstine, Uppsala (SE); Johan Ohman, Uppsala (SE); Philippe Busson, Uppsala (SE); Ronnie Palmgren, Uppsala (SE); Klas Allmer, Uppsala (SE); John Daicic, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 401 days.

(21) Appl. No.: 13/813,800

(22) PCT Filed: Apr. 28, 2011

(86) PCT No.: PCT/SE2011/050525
§ 371 (c)(1),
(2), (4) Date: Feb. 1, 2013

(87) PCT Pub. No.: WO2012/018294
PCT Pub. Date: Feb. 9, 2012

(65) Prior Publication Data
US 2013/0131323 A1    May 23, 2013

Related U.S. Application Data

(60) Provisional application No. 61/370,878, filed on Aug. 5, 2010.

(51) Int. Cl.
| | | |
|---|---|---|
| *C07K 16/00* | (2006.01) | |
| *G01N 30/56* | (2006.01) | |
| *C07K 1/14* | (2006.01) | |
| *C07K 1/18* | (2006.01) | |
| *C07K 1/20* | (2006.01) | |
| *C07K 1/22* | (2006.01) | |
| *B01D 15/20* | (2006.01) | |
| *B01D 15/22* | (2006.01) | |
| *G01N 30/60* | (2006.01) | |

(52) U.S. Cl.
CPC .......... *G01N 30/56* (2013.01); *B01D 15/206* (2013.01); *B01D 15/22* (2013.01); *C07K 1/14* (2013.01); *C07K 1/18* (2013.01); *C07K 1/20* (2013.01); *C07K 1/22* (2013.01); *G01N 30/6069* (2013.01); *G01N 2030/562* (2013.01)

(58) Field of Classification Search
None
See application file for complete search history.

(56) References Cited

FOREIGN PATENT DOCUMENTS

| EP | 2 196 471 | 6/2010 |
|---|---|---|
| WO | WO 02/062827 | 8/2002 |
| WO | WO 02/090372 | 11/2002 |
| WO | WO 2005/113147 | 12/2005 |
| WO | WO 2008/045505 | 4/2008 |
| WO | WO 2009/017491 | 2/2009 |
| WO | WO 2010/030222 | 3/2010 |
| WO | WO 2011/076386 | 6/2011 |

*Primary Examiner* — Yunsoo Kim
(74) *Attorney, Agent, or Firm* — Wood IP LLC

(57) ABSTRACT

The invention relates to a system and method for the stable storage of sensitive biological or chemical target substance, in a bound form on certain capture media. The method comprised providing a sample containing the target substance in a suitable buffer; combining the sample with a capture media to effect reversible binding of the target substance to the capture media; and storing the capture media with the target substance at between about −20 and 20° C.; and recovering the target substance from the capture media. The target substance recovered maintains the desired activity. Also provides are methods for reducing aggregates in the sensitive biological or chemical target substance.

30 Claims, 8 Drawing Sheets

% dimer polyclonal human IgG at

% dimer mAb2 at pH

METHOD FOR STORAGE AND STABILIZATION OF A TARGET SUBSTANCE

CROSS-REFERENCE TO RELATED APPLICATIONS

This application is a filing under 35 U.S.C. 371 of international application number PCT/SE2011/050525, filed Apr. 28, 2011, published on Feb. 9, 2012 as WO 2012/018294, which claims priority to U.S. provisional patent application No. 61/370,878 filed Aug. 5, 2010; the disclosure of which is incorporated herein by reference in its entirety.

FIELD OF THE INVENTION

The present invention relates to a system and method for the storage of a target substance. More specifically, it relates to a system and method for the stable storage of sensitive biological or chemical target substance, in a reversibly bound form on certain capture media. Also provides a method for reducing aggregates in the sensitive biological or chemical target substance.

BACKGROUND OF THE INVENTION

It is typical in production of a chemical substance such as a pharmaceutical or biopharmaceutical that the production process involves a series of technically distinct steps or unit operations which occur in chronological order. The goal of such processes is to end up with a target substance purified to a requisite degree for the intended application. This is true for a protein enzyme intended for pharmaceutical application or one intended for use as an industrial catalyst. In many cases the unit operations may include separation or purification steps involving porous or other high surface to volume ratio media, and methods including chromatography or filtration. Such methods are often further defined in regard to target flow-through or target capture—the latter involving a situation where the flow of target substance in solution through a porous media is hindered by its noncovalent chemical interaction with the surface of the porous media. Examples of capture media type interactions include ion-exchange interactions involving charged chemical moieties on the media, hydrophobic interactions involving apolar or other hydrophobic groups, hydrogen bond interactions, van der Waals' interactions including pii-pii overlap interactions between aromatic groups on the media and the target, "mixed mode" interactions where more than one of the above interactions occurs in a controlled manner due to the media possessing ligands offering more than one interactive groups or mixtures of different ligands offering different interactive groups, and affinity interactions. The latter may include boronate-carbohydrate affinities, metal ion affinities for chelating groups, or protein affinities for target substances such as avidin protein for biotin, or protein A for Fc regions of antibodies or other proteins. Affinity interactions typically involve mixed mode interactions with some defined molecular structure serving as the basis for the interaction. As such, affinity interactions are often the strongest noncovalent interaction involved in capture of protein or other biopolymers by porous media such as chromatography or filtration media.

What the above interactions have in common is that they bind target in a manner that localizes it in essentially native hydrated form at the surfaces of media. The media does not have to be porous to effect such capture however porous, capillary bed or other large surface area media allow such interactions to bind a significant amount of target per unit media volume (e.g. milligram per milliliter). It is significant to note that proteins captured at porous media or other surfaces, via the above interactions, often display native enzymatic or other protein activity and so they cannot be considered to have undergone a significant physical change. What the above interactions also have in common is that they are reversible allowing native, hydrated material to be readily eluted (recovered) from the media via an alteration of solution conditions such as pH, conductivity, polarity, temperature, etc. which themselves are nondenaturing of target. It is not uncommon that such capture interactions are used to both purify a target, e.g. by selecting binding or elution conditions which favor target over contaminants. Such contaminants my include undesired forms of the target which differ in size, shape, chemical group structure as a result of incorrect production (including intracellular production) or being altered during the purification process via aggregation, denaturation, oxidation, deamidation or other such phenomena common during processing, storage and formulation (for a recent review see Stability of Protein Pharmaceuticals: An Update, Mark Cornell Manning, Danny K. Chou, Brian M. Murphy, Robert W. Payne and Derrick S. Katayama, Pharmaceutical Research, Vol. 27, No. 4, April 2010, pages 544-575). It is also true that proteins or other targets captured on porous media can be recovered (eluted) at concentrations similar to their concentration on the media. Thus capture is often used to concentrate as well as purify a target.

It is typically desirable, from the perspectives of reducing costs or contamination, to produce substances such as pharmaceuticals, biopharmaceuticals or industrial/diagnostic enzymes in as short a time as possible. However in many instances one may wish to delay process time and consciously insert "hold" or "storage" points into a process. There may be several reasons for doing so. For example in the potential future production of metric ton amounts of antibody biopharmaceuticals it is understood that there may be significant cost advantages to running smaller scale purification strategies on a more-or-less continuous production regime rather than one large scale shorter term campaign (e.g. Very Large Scale Monoclonal Antibody Purification: The Case for Conventional Unit Operations, Brian Kelly, Biotechnol. Prog. 2007, volume 23, pages 995-1008.; see also Review: Future of antibody purification, Duncan Low, Rhona O'Leary, Narahari S. Pujar, Journal of Chromatography B, 2008, volume 848, pages 48-63). Such production methods would supposedly also benefit production of targets for non-pharmaceutical applications such as industrial biocatalysts.

It is also possible that in order to meet such production requirements that standard methods such as chromatography or filtration might be augmented with other methods such as precipitation or crystallization (e.g. Low et al. above; see also Alternatives to Chromatographic Separations, Jorg Thommes and Mark Etzel, Biotechnol. Prog. 2007, volume 23, pages 42-45). However the latter two methods may alter target in an undesired manner (e.g. aggregate formation)

and, perhaps more importantly, require significant dilution in specific (e.g. low conductivity) solutions to dissolve the crystals or precipitates and recover the target in hydrated soluble form. In this, such methods present drawbacks similar to the widely used protein storage methods of freeze drying, or freezing in solution. As such they are not as compatible as, for example, adding additional capture chromatography or filtration steps to a standard process already involving chromatography or filtration. This difference is significant as there are many instances where one may wish to hold up or otherwise delay one part of the process of producing a biopharmaceutical or similar target. And such instances are increasing. The example of a large mass antibody fermentation being processed in intermediates was noted above. Another example could be where a process is halted for a relatively short period of time, say overnight, to support lower labor costs by eliminating use of a night shift, or to accommodate an "off line" quality control measurement related to a validation required before further processing. So too, consider the case where purified biopharmaceutical is subjected to different types of polishing in order to facilitate different types of formulation (e.g. fluid versus solid formulation) so that target from the same lot can be used in different applications. Another example of emerging importance is the possibility of a biopharmaceutical or other drug being processed to certain degree of purity at one site and then further processed or formulated at another site. Such sites might be separated by a few tens of meters, a few kilometers, or even a few thousand kilometers. In the latter case the target substance may need to be transported in a format which allows it to be uncoupled and taken "off line" from the process line under sterile conditions, transported long distances under controlled conditions and rapidly reintroduced into the process line.

Today the most common approaches to interim storage of proteins and similar targets involve freeze drying or freezing in solution (see references above, e.g. Manning et al.; and those noted below) which alter the target in terms of its normal active and hydrated state, can effect varying degrees of denaturation, and are often time consuming both in preparation of the target for stabilization and storage and resuspending the target in solution to allow for further processing. Such methods also typically involve adding additives to reduce aggregate formation or chemical alteration of target during storage processing, and which may complicate formulation or even need to be removed later by additional processing prior to formulation.

FIG. 1 provides overview of typical recombinant biopharmaceutical production process and notes major process areas such as clarification, purification, polishing, formulation and delivery. Such an overview applies to a wide range of targets including biopharmaceuticals, plasma derived proteins, industrial enzymes, diagnostic enzymes, etc. The figure also notes three different places where there may be a need to hold up a process while maintaining a protein or other target capable of "capture" in a stable state. It is expected that the need for longer storage stability times may increase the closer one moves from crude preparation to bulk drug substance for formulation. In truth these three examples represent a broad spectrum of needs. What is important to note is if in a process one wishes to stop processing of a protein biopharmaceutical for say four to eight hours it may be difficult to accommodate this need by time consuming operations such as freeze drying or freezing.

In the case of freezing it involves taking the protein off line in a solution, adding cryoprotectant additives, freezing down with slow temperature cooling to not denature the protein over five to six hours. When the storage period is over it requires an additional five to six hours to thaw the protein sample and reintroduce it to the process line. Of course when dealing with significant amounts of target freeze-drying and resuspension may require even longer periods of time than freezing and potentially offer even more complex challenges in regard to target alteration or denaturation. In such cases the storage operations, not the desired storage time, negatively impact the potential economic or other benefits of such storage, limiting the ability of the operator to design a flexible and more economic process. This is especially true if additional steps and quality control analyses must be performed to remove, and verify removal of, the stabilizing additives prior to formulation.

One of the most significant challenges faced in production and storage of protein targets is microaggregate formation, in part as such aggregates can induce immune mechanisms that limit efficacy of the biopharmaceuticals. (e.g., Protein Aggregation and Its Inhibition in Biopharmaceutics, W. Wang, Int. J. Pharmaceutics, 2005, volume 289, pages 1-30). Interestingly aggregate formation is still a major challenge even though more is known about formation of such aggregates and their link to other phenomena such as protein denaturation during processing and storage (e. g. above review by Manning et al.). Thus a recent patent filing (Amgen US 2010/0056765) provided various additive mixtures to "inhibit protein aggregate formation induced by physical stresses associated with processing, manufacture, shipping and storing protein solutions, particularly freeze/thaw stress" and noted that "additives to stabilize proteins (during free/thaw operations) suffer from certain disadvantages, for example, the necessity of additional processing steps for additive removal. Further, none of the processes described in the art is suitable for stabilizing proteins during repeated freezing and thawing processes such that no . . . aggregates are formed during the manipulation." It is important to note that aggregates of identical proteins often occur over broad range of sizes from dimeric protein forms (two proteins self associated) to micron sized aggregates of large numbers of protein molecules but that typically presence of dimers suggests unstable storage or other conditions which will also give rise to larger aggregate forms.

While it is true that polymer based precipitation (flocculation) of proteins appears to maintain them in stable form regarding aggregate formation and such precipitates might be useful in regard to some types of purification storage and formulation (e.g. Millipore US 2009/0232737; Biogen IDEC WO2009/051726, Amgen WO 2009/026122, Genentech US 2008/0193981) such methods still come with the drawbacks noted above.

No storage method is known which is capable of not only holding aggregate levels stable but also reducing aggregate levels.

It is well recognized that modern bioprocess separation media including chromatography media, monolithic media, filtration media often do not denature proteins over the time scales of most separation operations—typically less than 12 hours. The benign effect of such media is recognized even when proteins are covalently localized at the surfaces of such media including agarose based media. (e.g. Glyoxyl agarose: A fully inert and hydrophilic support for immobilization and high stabilization of proteins, C. Mateo et al., Enzyme and Microbial Technology, 2006, volume 39, pages 274-280.). It has recently been noted that proteins can be affinity bound to porous or other media and then stabilized by partial or total drying of the protein bound matrix at temperatures 18 to 42° C. (WO 2009/034204). The reason for stable storage of the unhydrated protein is unknown but may be related to its complexation by polymers on the matrix in manner similar to what occurs in dehydrated polymer-protein precipitates. This may be similar to storage of proteins by drying them sugar solutions such as available in commercially supplied formulations (e.g. READY-TOGO™ reagents from GE Healthcare). Use of such technology for large-scale protein production would be hindered by the need to dry (and later rehydrate) the protein in controlled manner and need for specialized equipment.

Therefore, there is a need for an improved method for stable storage of sensitive biological or chemical target substance in hydrated form so that rehydration and solubilization is not required. There is also a need for a method to effectively reduce aggregates for such target substance.

SUMMARY OF THE INVENTION

The present invention provides an improved method and system for the storage of a sensitive biological or chemical target substance, in a bound form on certain capture media. The invention also provides a novel method and system for reducing aggregates in sensitive biological or chemical target substance. It has been discovered that it is possible to effect storage and stabilization of protein solutions from aggregate formation (and thus supposedly related physicochemical phenomena) by storing the protein in hydrated and active form on capture media. Although the format studied was chromatography media in a column, capture filtration or other formats would also function, where the target can be readily captured and stored, without need for adding stabilizing additives, in manner providing better stability than freezing. In addition to holding aggregate levels stable the method can be used to reduce aggregate formation such that in some cases during storage samples undergo reversal of aggregation so as to yield more monomer than was applied to the column. Such column or other capture formats may be used in any known storage regimes and is a flexible approach ideal for a variety of conditions from short-term local storage to longer term transport related storage. A wide variety of capture media and base matrices are capable of such functions.

Although experiments below have only involved dedicated commercially available media, the work can be extended to media or mobile phases specifically designed to optimize storage challenges related to specific applications (e.g. oxidation, deamidation). In the latter case the stabilizing additives may be flushed from the column prior to elution of target thus easily and effectively eliminate concerns when stabilizers, including precipitating polymers, are added to target containing solutions. In addition various additives often included in storage solutions protect protein or other targets, including neutral or charged hydrophobic polymers, as well as reducing agents, etc. could be included covalently in capture media used to capture and hold proteins in stable storage. The advantage being that when the target is eluted from the column it would also be separated from the column bound stabilizing agents. Thus for example polymer modified capture media could be used to reproduce stabilizing conditions similar to those found in polymer-protein precipitates or flocculants. However the media associated stabilizing agents would be included in a manner free of concerns for contamination of eluted target. It also appears that capture media packaged in columns or other formats can be specifically adapted for sterile applications. This could include pre-sterilized media, media fitted with sterile couplings, columns fitted with solid state temperature, pH or other sensors.

Thus, in one aspect of the invention, it is provided a method for storage of a target substance. The method comprises providing a sample containing the target substance in a suitable buffer; combining the sample with a capture media to effect reversible binding of the target substance to the capture media; and storing the capture media with the target substance reversibly bound thereto at between approximately −20 and 20° C. for a desired amount of time; and recovering the target substance from the capture media. The target substance recovered maintains the desired activity.

Another aspect of the invention provides a method for reducing aggregates in a solubilized target substance sample. The method comprises providing a sample containing the target substance in a suitable buffer; combining the sample with a capture media to effect reversible binding of the target substance to the capture media; storing the capture media with the target substance reversibly bound thereto, at between about −20 and 20° C., for at least an amount of time which allows a significant amount of aggregates of the target substance to separate into monomeric form; and recovering the target substance from said capture media. The target substance recovered contains a significantly reduced amount of aggregated form of the target substance, and maintains the desired activity.

DETAILED DESCRIPTION OF THE INVENTION

Figure 1:
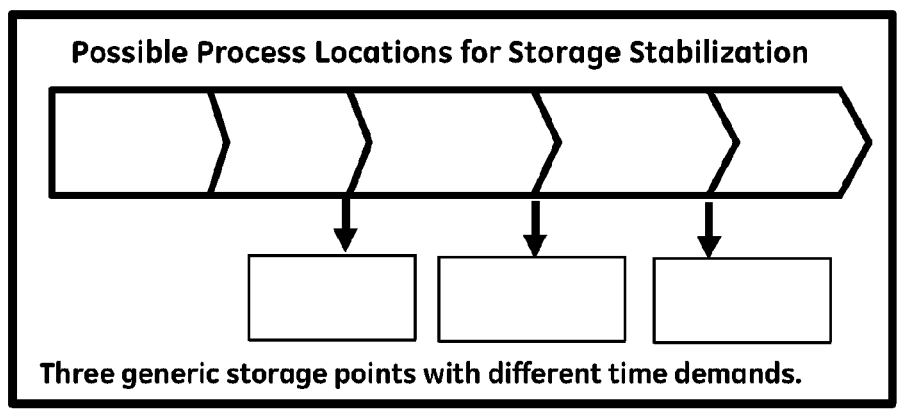
FIG. 1 shows the possible process locations for storage and stabilization.

Certain aspects of the invention provides storage and stabilization of sensitive chemical or biological target substances such as biopharmaceutical targets adsorbed or otherwise captured in non-covalent manner at insoluble media (e.g. chromatography bead, filter, monolith, capillary) surfaces. The storage and stabilization can be further defined (by duration, storage temperature and existing methods) in regard to three customer needs which often occur in a generic bioprocess work flow from fermentation→clarification→purification→polishing→formulation. The three related areas are: A. Short term (hours to one or two days) room temperature or 4° C. storage in stable form during processing—typically to add flexibility in purification regimes, or between processing and polishing. B. Intermediate term (days to week) storage at room temperature or 4° C.—often for bulk drug substance between polishing and formulation—and to support processes which are performed at significantly different times. C. Longer term (days to months) storage of bulk purified drug substance, or even as bulk formulation, e.g. proteins plus stabilizing additives in solution. The latter is often done in frozen or lyophilized format with added substances (e.g. trehalose, ethylene glycol, polyethylene glycol polymer, or polysaccharide polymer) which enhance stabilization but may not enhance efficacy. Further, B and C may be performed to support process flexibility or transport between different plants or even regional or international locations.

The methods and system for storage and stabilization provide a number of advantages which include but not limited to:

1. Maintaining target material "on-line" in column adsorbed (but not covalently modified) format. In this format target can also be easily taken off-line and then brought on-line simply by coupling or uncoupling the column
2. Maintaining target in essentially normal hydrated state similar to solution for intermediate storage at room temperature or 4° C.—instead of frozen, lyophilized, precipitated, crystallized or other state involving taking the target off-line and altering its normal hydration. An added benefit is the greatly reduced processing time since no extra processing step (e.g. freezing then thawing) is required.
3. Reduction or elimination of stabilizing additives which in other approaches need to be added and then often need to be removed from final product via extra post-storage processing steps. As an example, the use of polymer tether media replaces the need of adding polymer stabilizers. As another example a reduced carboxymethyl ligand could replace the need for stabilizing agents to combat oxidation.
4. Ease of transportation in column or bag format in manner that allows direct coupling into downstream column based bioprocess (no thawing, re-dissolving).
5. Physical state of the resin is maintained and resin can in some cases be cleaned and reused.
6. Target on capture media is maintained in 10 to 200 g/L desired range for formulation providing ease of use in boundary between capture, polish and formulation.
7. Interfaces directly with other separation methods since the protein or other target is applied directly to storage column in standard buffer. In some cases this buffer can be the elution buffer used to recover target from a previous processing step. For example lower conductivity elution buffer related to a hydrophobic interaction chromatography step could be used as adsorption (capture) buffer for a follow on ion exchange related storage media.
8. The target when stored in capture mode on column is amenable to on the column sterilization and enzymatic or chemical modifications with the reagents involved in the treatments passing through the column
9. Can be provided sterile (or in dried bead format) on e.g. READYTOPROCESS™ (RTP) columns, dye indicator or other inexpensive sensors, which are modified with temperature, pH or time logging via RFID or optical dye sensors.
10. Can be used in non-column formats (e.g. capture filters, monoliths or beads in bag, coated capillaries, etc.).
11. Can effect improvement in target sample quality via either active manner on support (reversing certain events such as aggregation) or during loading or elution (e.g. when it might be possible to isolate aggregates or other proteins). Latter could be due to various chromatographic effects or simple column SEC effects based on storage media pore size distribution, or by addition of filter to the column.

12. In certain cases (for example if the media was based on dextran polymer with biodegrading linkages) the storage colloid particle media could serve as the delivery media for drug delivery, especially for topical applications, or, e.g. when the drug is stored in a syringe packed with the media.

One aspect of the invention provides a method for storage of a target substance. In this aspect of the invention, the target substances recovered maintain the desired activity. Another aspect of the invention provides a method for reducing aggregates in a target substance. For certain target substances, not only do the target substances maintain the desired activity, a significant amount of aggregates present in the initial sample separate into monomeric form of the target substance. The mechanism of this is unknown but believed to be related to the monomeric forms offering greater (capture) binding interaction possibilities than dimeric or multimeric forms. As a result monomeric forms can be more energetically favorable on column though transition back to monomeric forms may be related to kinetics more favorable to storage than chromatographic separation time intervals.

In one embodiment, the target materials can be proteins, peptides, oligopeptides, oligonucleotides, RNA, DNA, protein vaccine, virus vaccine, and other sensitive therapeutic substances. In a preferred embodiment, the target material is monoclonal or polyclonal antibody. In certain embodiments, the target material is a mixture of several kinds of substances, so long as they reversibility bind to the capture media. For example, the target material can be a plasma protein mixture, each component protein capable of reversible binding to the capture media. It could also be a mixture of proteins which function together such as in an enzymatic cascade. Alternatively, the target is a fusion protein, or other recombinantly modified target material. The target can also be a polymer modified protein or other covalently modified target material.

In another embodiment, the target material, when first combined with the capture media, is at a concentration of about 1 to 300 g/l (mg/ml) volume, preferably 10 to 200 g/l volume; such ranges reflecting the wide ranges of both possible adsorption and formulation concentrations related to various drug substances.

In still another embodiment, the target material, while bound on the capture media during, is in a hydrated state similar to that when in solution.

In one embodiment, the sample containing the target material is a cell culture supernatant, cell culture lysate, bacterial culture supernatant, bacterial culture lysate, blood, plasma, or other body fluid in either native or previously processed state. The target containing fluid may be manipulated in regard to alteration of pH, conductivity or other parameters to enhance target binding and stabilization on the capture media.

The target containing fluid may be manipulated by the operator in regard to alteration of pH, conductivity or other parameters to enhance target binding and stabilization on the capture media. However the range of media and binding conditions found to be effective (see below) suggest that one advantage of the present approach is that such manipulation would not be complicated or involve significant (i.e. 10 fold or more) dilution of target containing solution. As such it would be amenable to high throughput modeling such as in microtitre plate based experiments.

In certain embodiments, the capture media is a matrix with a high surface area to volume ratio such as found in spherical chromatography particles which are solid, in terms of not allowing target to diffuse into their interiors and have a mean diameter of 50 microns or less. They may also have diameters of 1000 microns or less and be porous with such pores allowing diffusion of target substance into the particle. Commercial available porous media examples are found in the experimental results noted below.

In certain embodiments, the capture media comprises packed bed or fluidized bed chromatography particles, porous monolith, capillary bed or filter bed and which provide for target binding at a capacity in excess of 1 gram per liter volume. Again the pores of such formats would allow diffusion of target and reversible binding at relatively high concentration.

In certain embodiments, the interactions involved in target capture (reversible binding between the target substance and the capture media) include ion-exchange, cation-pi, pi-pi, hydrogen bonding, metal ion affinity, hydrophobic interaction, or combinations of such interactions via mixed mode or affinity interactions. Combined mixed mode interactions can include for example those related to different matrix groups (e.g. in case of hydroxyapatite). They can also include single molecular entities capable of different interactions—such as aromatic groups capable of hydrophobic and pi-electron related binding interactions. Affinity interactions can include a. boronate containing substances affinity for glyco-containing compounds, b. protein A and derivatives with affinities for antibody Fc groups, c. other protein "ligands" such as protein L which binds to other antibody regions, biotin binding proteins, cellulose binding proteins, albumin binding ligands, or other ligands used in affinity separation media. It can also include less scientifically defined interactions such as "induced charge", "high salt tolerant ligand" and other interactions related to common capture media.

The capture media can be formed using a wide variety of insoluble substances such as those typically used to construct bioseparation media including chromatography media, monolithic media, and filtration media. In certain embodiments, the capture media includes a synthetic or biological polymer component. Thus there is provided a synthetic (e.g. acrylamide, or polyether) or biological (e.g. dextran or agarose) polymer component to the target-matrix interaction resulting from naturally occurring polymers on the matrix, or polymers the matrix has been chemically modified with. Such polymers can be used to enhance hydration of the matrix and captured targets or otherwise help maintain targets in native (non-denatured, non-chemically-modified, non-aggregated) state. Such polymers may naturally contain ion exchange, mixed mode, or other target capture groups. They may also be modified, either before or after matrix localization, with target capturing groups or ligands allowing both enhanced hydration of polymer (and hence matrix and captured target) and enhanced target capture. The enhanced target capture can be a result of polymer tethered ligands' being capable of increased interacting with target substance in a manner that is nondenaturing, nonchemically modifying, and nonaggregating. In regard to the latter it might maintain aggregate levels or promote a reduction in aggregate levels.

In one example, the polymers on the capture media are dextran containing polymers. These polymers (e.g. dexran or dextran sulphate or dextran carboxymethyl) are medically recognized drug formulation excipients, thus reducing concerns related to processing transitions between purification and polishing and formulation. Other polymers may include native or secondarily modified starch polymers such as hydroxyethylstarch, or polymers containing ethylene oxide groups such as such as poly(ethylene glycol). The role of additional polymer or ligands is not only to capture but to reduce unwanted chemical interactions (oxidation, reduction, deamidation) and to lower the freezing point of the water on the matrix.

In certain embodiments, the capture media is CAPTO™ MMC, CAPTO™ S, CAPTO™ Adhere, CAPTO™ Q, MABSELECT™, CAPTO™ Phe high sub (hs), pH responsive hydrophobic interaction chromatography (pH HIC) media. The above media typically reflect different ligand surface treatments on highly cross-linked porous agarose chromatography media. Other cross linked agarose media are various types of SEPHAROSE™ media such as SEPHAROSE™ Fast Flow or SP SEPHAROSE™ High Performance. Other types of media include media on cross linked dextran matrices or MACROCAP™ (cross linked acrylated dextran) media. Other cross-linked bioprocess media including that based on cross-linked methacrylate, cross-linked divinylbenzene, cross-linked polystyrene, as well as ceramic, or hydroxyapatite or glass. In some cases polymers may be added as surface treatments such as use of dextran polymer surface layers on agarose media as in SEPHAROSE™ XL media. There is, of course, a wide variety of other bioprocess media based on acrylated or even glass porous matrices in case of porous particles, or cellulose or polyvinylsulfone or other polymers in the case of filters. What all of these media have in common is that they are formed using cross-linked polymers to which various ligand or other chemical groups can be covalently attached, and which are capable of capturing proteins and other targets in nondenaturing, biocompatible manner (noted above) necessary to function in the present invention. Of course such polymers can also be used to form filters, monoliths, or other solid phase capture surfaces, or used to develop coatings which can be applied to glass, plastic or other materials to provide the capture formats capable of functioning per the present invention.

In a preferred embodiment, the capture media is mixed mode media CAPTO™ Adhere. In an alternative embodiment, the capture media is the protein ligand based affinity media MABSELECT™. In certain embodiments, the capture media is a mixture of two or more media. Alternatively, the capture media includes more than one reactive groups or more than one ligand, and is capable of interacting with and binding more than one kind of protein.

In certain embodiments, the reversible binding between the capture media and the target substance is by charge, hydrophobic, hydrogen bond, van der Waals, mixed mode, or other reversible chemical interaction, and the target substance is not denatured throughout the method.

In certain embodiments, the sample and the capture media are combined in a container selected from column, bag, tank, cassette or other housing, to effect reversible binding of the target substance to the capture media in a user friendly manner. In certain embodiments, the capture media is in a small column such as a syringe. In certain embodiments, the container is capable of supporting the binding between the target substance and the capture media, as well as the storage of the bound capture media before recovering of the target substance from the capture media. In a preferred embodiment, the container is a chromatographic column. In another preferred embodiment, the container is a transportable housing. In certain embodiments, the container withstands freezing to at least −20° C.

In certain embodiments, the capture media with the target substance reversibly bound thereto is stored at a temperature between about −20° C. and about 20° C. For example, the capture media with the reversibly bound target substance is stored at about −20° C., 4° C. or 20° C. It is not inconceivable that in special circumstances the containers may have to store target at higher or lower temperatures, e.g. −80 to +40° C., and protect target in better than or equal manner than if stored in aqueous buffer under similar conditions.

In certain embodiments, the capture media with the target substance reversibly bound thereto is stored for from less than 2 weeks to several months. In one embodiment, it is stored for less than 2 weeks. In another embodiment, it is stored for about 2-4 weeks. In yet another embodiment, it is stored for more than 4 weeks. In another it is stored for 48 hours or less. These times are related to different possible applications, occurring in different parts of generic processing path, and related to different targets, as noted above.

In certain embodiments, the target substance recovery after the storage step includes eluting the target substance from the capture media and collecting the eluent containing the target substance.

It is noted that certain optimizations of the methods can be realized by routine experimentation. For example, the storage conditions can be optimized by high throughput screening methods with various buffers chosen according to known binding and elution parameters such as conductivity, pH and salt type. In regard to the latter buffer salt or salt mixture combinations may be chosen in regard to the well known ability of certain Lyotropic Series or Hoffmeister Series salts to better stabilize proteins and other targets.

The methods and systems may enable the integration of polishing step and storage (via media). They further enable discontinuous processing of the target, as it is possible to physically alter the disposition of the matrix containing housing/container in regard to connection with other equipments, so as to isolate, transport or store the target for a desired period of time. One examples of such disposition would be in regard to use of sterile columns or sterile connectors to preserve sterility, as well as dark columns to enhance storage and stabilization of UV-sensitive targets. In another example stabilizing and storage columns could be used in conjunction with more advanced capture paths such as manifold connected multiple columns, or simulated moving bed multiple column set ups, so that the columns could be more fully loaded with target and more readily placed on-line or taken off-line without compromising process sterility. In regard to the latter it might facilitate varied formulation at different sites such as for biopharmaceuticals which will be partly formulated as purified and partly modified for other applications. Examples of the latter include the many biopharmaceuticals which today are used in generic form and also in polymer modified form (e.g. ROFERON® and PEGASYS®, or NEUPOGEN® and NEULASTA®).

The methods and systems enable the stabilization of a sensitive target such as a protein in a media for high-throughput screening purpose. They also enable the stabilization of sensitive target for forensic, or home-test, or diagnostic or clinical applications e.g. collecting/storage of biological fluids (e.g. blood) which contain sensitive target material that are suitable for stabilization by the methods described above. Thus, in addition to utility in large scale bioprocess applications such as drug manufacturing, the methods and systems are also suited for clinical and analytical, as well as research, applications.

In carrying out the methods described it is to be understood that reference to particular buffers, media, reagents, cells, culture conditions, pH and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein. It will be readily apparent to one skilled in the art that varying substitutions and modifications may be made to the invention disclosed herein without departing from the scope and spirit of the invention.

EXAMPLES

The inventors hypothesized that certain capture media may stabilize sensitive biological or chemical target substance such as proteins against degradation during storage, compared with storing in solution, for periods longer and conditions more unusual than typical of chromatographic operations. The following examples focus on storing human antibodies in solution or on various gel media during a certain time period to study the effect on stabilization and aggregate formation. The goal was to find gel media that keep the activity while keep or improve stability of the antibodies compared with freezing and thawing (concerning formation of soluble aggregates i.e. to minimize aggregate formation). One reason for focusing on aggregation is that it presents a significant commercial and biomedical challenge. Another is that aggregate formation is often linked with, and therefore indicative of, protein shape or chemical alterations (i.e. see Protein Aggregation and Its Inhibition in Biopharmaceutics, W. Wang, Int. J. Pharmaceutics, 2005, volume 289, pages 1-30). As such media which stabilizes against dimer and larger aggregate formation is expected to stabilize against other protein alteration. Although dimer formation and related more significant aggregation is a general problem in protein biotherapeutics it is particularly noteworthy in antibody formulations due to the large size, varied surface structure and typically high purification and formulation concentrations related to such targets (e.g. see W. Wang above ref).

Potential gel media for the studies are shown in table 1.

TABLE 1

Candidate Experimental and Control Media.

| Candidate Media | Matching Control Media | Media Design Focus |
| --- | --- | --- |
| SUPERDEX ™ | SEPHADEX ™ | Neutral Dextran for SEC |
| SP XL or CAPTO ™ S | SP FF | Dextran tether for CEC |
| Q XL or CAPTO ™ Q | Q FF | Dextran tether for AEC |
| CAPTO ™ Adhere | TBD | Mixed Mode |
| MMC | TBD | Mixed Mode |
| pH HIC on HP | CM HP, Butyl HP | Mixed Mode with polymer tether |
| CAPTO ™ Phe is | CAPTO ™ Phe hs | HIC Media of low and high hydrophobicity |
| MABSELECT ™ (NPA) | Protein A FF | Ig affinity media of varied capacity |

All media is commercially available from GE Healthcare.

1. Experimental 1.1 Materials/Investigated Units 1.1.1 Materials

| Gel media | Article no./lab. notebook prototype number* | Lot no. |
| --- | --- | --- |
| SUPERDEX ™ 200 prep grade | 17-1043-02 | |
| SEPHADEX ™ G-50 medium | 17-0042-01 | |
| CAPTO ™ MMC | 17-5317-10 | 10034224 |
| CAPTO ™ S | 17-5441-10 | 10023850 |
| SP SEPHAROSE ™ FF | 17-0729-01 | 306691 |
| SP SEPHAROSE ™ XL | from 1 ml HITRAP ™ | |
| CAPTO ™ Adhere | 17-5444-10 | 10037127 |
| CAPTO ™ Q | 17-5316-10 | 10019885 |
| Q SEPHAROSE ™ FF | 17-0510-01 | 306634 |
| Q SEPHAROSE ™ XL | from 1 ml HITRAP ™ | |
| nProtein A SEPHAROSE ™ 4 FF | 17-5280-01 | 10032389 |
| MABSELECT ™ | 17-5199-01 | 10019356 |

-continued

| Gel media | Article no./lab. notebook prototype number* | Lot no. |
|---|---|---|
| Butyl SEPHAROSE ™ High Performance (HP) | 17-5432-01 | 10006865 |
| CAPTO ™ Phenyl high substitution | H.N. | 100277060 |
| CAPTO ™ Phenyl low substitution | 1707-075B H.N. | |
| SEPHAROSE ™ HP 16% AMBN | U1367059 | |
| pH HIC HP 2%** | U2283084 G.H. | |
| pH HIC HP 4% AMBN** | U2283089 G.H. | |
| pH HIC HP 6% AMBN** | U2283085 G.H. | |

*All the above media are from GE Healthcare, Uppsala, Sweden. Commercial media noted by catalogue (e.g. 17-XXXX-XX) number include trade names SEPHADEX ™, SUPERDEX ™ SEPHAROSE ™ FF, SEPHAROSE ™ XL, MABSELECT ™ and CAPTO ™. CAPTO ™ Phenyl and pH HIC media are available via Custom Designed Media. Prototype variants typically noted by prefix U (i.e. U1367059). The different gel media were diluted to 20% slurry concentration with 20% ethanol prior to use in 96-well MULTITRAP ™ plates or SPINTRAP ™ columns.

**The pH responsive HIC (pH HIC or pHIC) media used in the present studies was obtained from the Custom Designed Media group at GE Healthcare (Uppsala, Sweden). It is a polymeric coating applied or generated at the surface of an existing base matrix - in the present studies SEPHAROSE ™ High Performance (HP). General synthesis of the media is detailed in WO2004/082801. It is a copolymer of three different functional groups, N-isopropyl acryl amide (NIPAAm), acrylic acid (AA) and butyl acrylamide (BAA). The latter can be in linear or tert-butyl form (t-BAA). NIPAAm provides for "hydrophobic effect" driven self association at temperatures above critical temperature (typically in range 30 to 40° C. depending on solution conductivity and other operating conditions). For a general review of biomedical uses of such polymers see Stimuli responsive polymers for biomedical applications, Carolina de las Heras Alarco'n, Sivanand Pennadam and Cameron Alexander, Chem. Soc. Rev., 2005, 34, 276-285, or Smart polymers: Physical forms and bioengineering applications, Ashok Kumara, Akshay Srivastavaa, Igor Yu Galaev, Bo Mattiasson. Prog. Polym. Sci. 32 (2007) 1205-1237. AA groups provide for polymers which alter hydrophobicity over pH range (4 to 8) suitable for chromatography of proteins. This shifts the self association responsiveness of the polymer from temperature to pH plus temperature. BAA, or the more chemically stable t-BAA used in the present media, tunes the performance of the media in regard to various chromatographic performance. Details of such media and its chromatographic performance have been presented in several scientific publications including K. Becker, E. Hallgren, E. Carredano, R. Palmgren, L. Bulow, J Mol Recognit 22 (2009) 104, K. Becker, J. Van Alstine, L. Bulow, J Chromatogr A 1202 (2008) 40. The pH HIC media used in the present studies consisted of the above polymer generated by copolymerisation in situ at SEPHAROSE ™ High Performance (HP) base matrix media surfaces. Different pH HIC media samples were studied which reflected ifferences in concentration (2%, 4%, 16%) of copolymerisation initiation agent ABMN per WO2004/082801.

1.1.2 Chemicals, Solutions and Equipment

| Chemicals/Solutions/Equipment | Lot no. | Supplier |
|---|---|---|
| GAMMANORM ®165 mg/ml, polyclonal human IgG | 5247118603 | Octapharma |
| mab2 human monoclonal antibody | 4507198602 | GEHC |
| 1M Tris-HCl pH 7.5 | 118218 | USB Corp. |
| Sodium Azide | K24467106 752 100 G | KEBO Lab. |
| PBS tablets, giving 0.14M NaCl, 2.7 mM KCl, 10 mM Phosphate pH 7.4 | 154501 | Medicago |
| Sodium Chloride | K40921504 014 | Merck |
| Ammonium Sulphate | A927017 905 | Merck |
| Sodium Acetate trihydrate | TA 935767 203 | Merck |
| EDTA plusone | K26458264 941 | GEHC |
| Sinapinic acid | | |
| Ethanol | | |
| Acetic acid | | |
| NaOH | | |
| PD ™-10 Columns | 386536 | GEHC |
| XK ™ 26 HiLoad 26/60 SUPERDEX ™ 200 pg | 204037 | GEHC |
| SUPERDEX ™ 200 5/150 GL (2 connected in series) | 10036165 | GEHC |
| MALDI target, stainless steel 384 | | Bruker |
| Syringe filter 0.2 μm | | Whatman |
| VIVASPIN ™ 6 MWCO 50000 | 09VS0640A | GEHC |
| UV plate 96 well | 21008042 | Costar |
| ÄKTAEXPLORER ™ | | |
| ÄKTA ™ micro | | |
| SPECTRAMAX ™ Plus 384 | | Molecular devices |
| Bruker AUTOFLEX ™ III | | Bruker |

1.2 Methods

1.2.1 Protein Concentration Determination

OD 280 nm of samples in a UV plate 96 well is measured on a SPECTRAMAX™ Plus 384 instrument. PBS buffer is used for blanking. PathCheck (SPECTRAMAX™ instrument feature) is used to normalize OD values to a 1 cm path length.

1.2.2 Full-Length Protein Analysis Using MALDI-TOF

Saturated sinapinic acid in 99.5% ethanol is used to seed a stainless steel MALDI target. Samples are mixed 1:1 with saturated sinapinic acid in 30% acetonitrile, 0.1% TFA in water. A protein mix (Bruker protein mix 2) is used for calibration. Use the LP_66 kDa method on the Bruker AUTOFLEX™ III instrument.

1.2.3 Aggregate Analysis Using SEC

Two SUPERDEX™ 200 5/150 GL columns are connected serially using a proper union. PBS is used as running buffer at a flow rate of 0.35 ml/min on an AKTA micro system. 10 μl of each sample is injected via the auto sampler. The built-in software is used for integration of the peaks. Retention volume is calibrated using a gel filtration calibration kit containing proteins with known molecular masses prior to analysis.

1.2.4 Protocol for Gel Media in MULTITRAP™ Plates

| MULTITRAP ™ protocol |
|---|
| Each step is followed by centrifugation using a swing-out rotor, 500 × g, for 1 minute unless incubation. |
| Add 100 μl 20% media slurry of each gel media to wells in triplicate in a MULTITRAP ™ 96 well filter plate, gives 20 μl media/well. Remove storage solution by centrifugation. |
| Equilibration |
| Add 3 × 200 μl equilibration/wash buffer to each well. Buffers according to each gel medias requirements. |
| Addition of antibody |
| Immediately after equilibration, add 20 μl of the antibody solution, prepared in appropriate buffer. Fully suspend the medium by mixing and incubate for several days/weeks at appropriate temperature. After incubation, add 20 μl equilibration/wash solution and then collect the remaining solution (flow-through). |
| Washing |
| Add 3 × 200 μl equilibration/wash buffer. |
| Elution |
| Add 40 μl of elution buffer and mix. Incubate 5 minutes. Perform this step two (2) times total. Collect eluate fractions one and two. |

1.2.5 Protocol for Gel Media in SPINTRAP™ Columns

| SPINTRAP ™ protocol |
| --- |
| Each step is followed by centrifugation using a EPPENDORF ™ centrifuge unless incubation. (300 × g, for 1 minute or 1000 × g during last wash step and elution). |
| Add 200 µl 20% media slurry of each gel media to individual SPINTRAP ™ columns in triplicate, gives 40 µl media/column. Remove storage solution by centrifugation. |
| Equilibration |
| Add 3 × 400 µl equilibration/wash buffer to each column. Buffers according to each gel medias requirements. |
| Addition of antibody |
| Immediately after equilibration, add 40 µl of the antibody solution, prepared in appropriate buffer. Fully suspend the medium by mixing and incubate for several days/weeks at appropriate temperature. After incubation, add 60 µl equilibration/wash solution and then collect the remaining solution (flow-through). |
| Washing |
| Add 2 × 400 µl equilibration/wash buffer. |
| Elution |
| Add 400 µl of elution buffer and mix. Incubate 5 minutes. |

2. Results and Discussion

2.1 Preparation of Start Material with Low Dimer Content

The GAMMANORM® polyclonal human IgG (Octapharma) samples, stored according to specifications in solution at 4-8° C., contained considerable amounts of aggregates according to size exclusion analysis (SEC) analysis. In order to better observe the reduction in aggregates in the latter experiments, we first prepared a test sample which is more sensitive—a start material with low levels of aggregates. This is in part because the aggregation level of the GAMMANORM® samples appeared to stabilize after storage in solution at 4-8° C. for a certain time (weeks to months, data not shown) depending on storage conditions.

Two preparative runs were done. GAMMANORM® was taken from ampoules and mixed with run buffer (50 mM Tris, 150 mM NaCl, pH 7.0 or PBS pH 7.4) to a final protein concentration of about 40 mg/ml which is representative of many bioprocess solutions during antibody processing.

Figure 2:
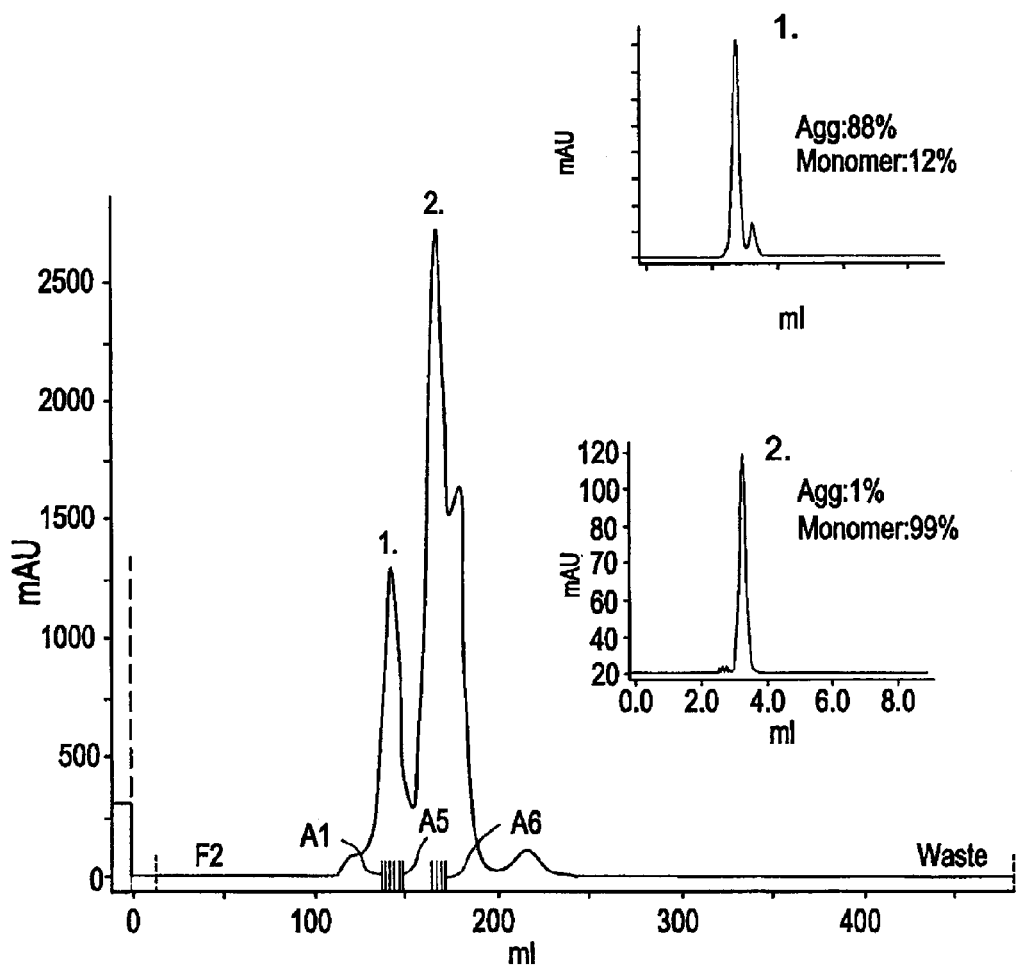
FIG. 2 shows the chromatogram from a preparative size exclusion chromatography (SEC) separation of polyclonal human antibody (GAMMANORM®, Octapharma). Analysis of pooled fractions, peak 1 and peak 2, are shown to the right. Antibody dimers (peak 1) elute before monomers (peak 2) in SEC.

Sample was loaded via a SUPERLOOP™ onto a HILOAD™ 26/60 SUPERDEX™ 200 pg column 5 ml of sample was loaded during the first preparative run and 25 ml was loaded on the second preparative run. The sample was eluted with run buffer at a flow rate of 2.50 or 2.65 ml/min. The result from the first preparative run is shown in FIG. 2.

2.2 Freeze Thaw Stress-Test of Antibodies Stored in Solution

It is known in general that repeated freeze/thaw cycles tend to increase protein aggregate formation. Other sources of protein aggregation are agitation, pH and temperature extremes. For extended storage, protein solutions are preferably frozen to protect the proteins from degradation by slowing the kinetics of various degradation processes. However fluctuations in thermal regulation, especially during transportation, can result in temperature fluctuation related stress. Such stress can also occur in research and analytical laboratories during transport or repeated testing of protein containing samples.

2.2.1 Quick Stress-Test of Human Polyclonal IgG

The first experiment used purified monomeric (single molecule) enriched sample of human polyclonal IgG containing 1% dimer according to SEC analysis. Three HPLC glass vials were prepared with sample mixed with different buffers, sodium chloride and water to get a final buffer concentration of 50 mM and a final sodium chloride concentration of 150 mM. The protein concentration was less than 10 mg/ml. The vials were put into a −20° C. freezer for one hour. The vials were taken out into room temperature (+20° C.) and the samples were allowed to thaw before SEC analysis. Results are shown in table 2. There was a significant amount of aggregation formation in the sample adjusted to an extreme pH just after freezing and thawing.

TABLE 2

Polyclonal human IgG at three different pH's, after freezing to −20° C. for one hour followed by thawing at room temperature.

| Vial/Sample | % monomer | % dimer | pH |
| --- | --- | --- | --- |
| 1 | 86.0 | 14.0 | 2.5-3.0 |
| 2 | 98.7 | 1.3 | 7 |
| 3 | 99.1 | 0.9 | 9 |
| Start material | 99.0 | 1.0 | 7 |

2.2.2 Quick Stress-Test of Human Monoclonal IgG

Figure 3:
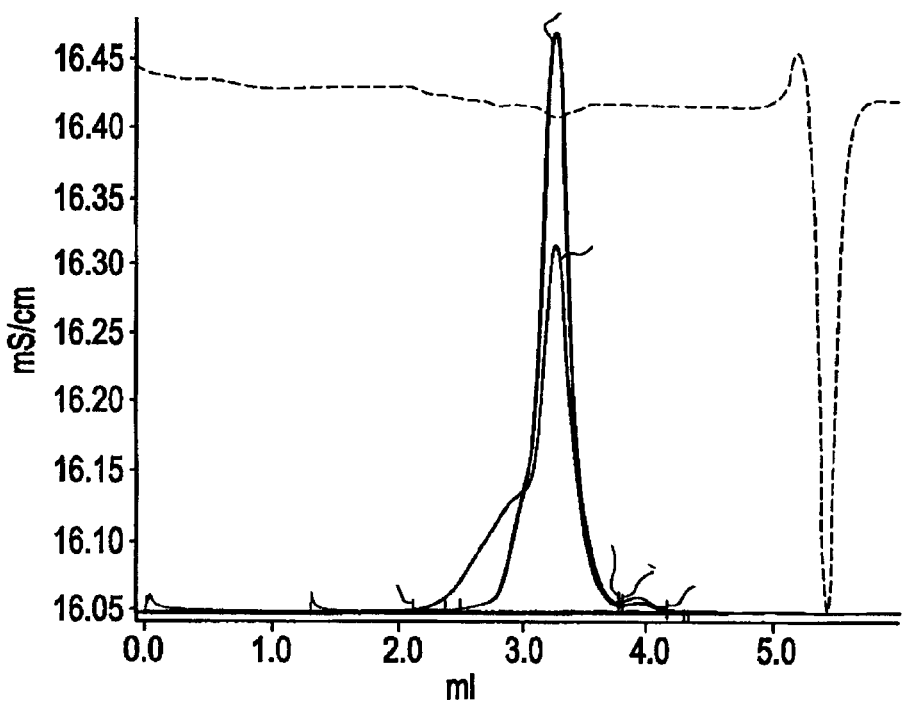
FIG. 3 shows SEC analysis of monoclonal antibody (mab2) samples after freezing and thawing at three different pH's. The three chromatograms are overlaid and the monomer peak has a retention volume of 3.26-3.27 ml. There is not enough dimer to exhibit a distinct peak however dimer related peak "shoulder tailing" is seen in front of the monomer peak.

Another experiment was performed using "mab2" (GE Healthcare internal laboratory designation) monoclonal antibody (21 mg/ml in PBS pH 7.4) as start material. Three HPLC glass vials were prepared with 50 µl start material mixed with different buffers, sodium chloride solution and water to get a final buffer concentration of 50 mM and a final sodium chloride concentration of 150 mM. The protein concentration was about 10 mg/ml. The vials were put into a −20° C. freezer for one hour. The vials were taken out into room temperature (+20° C.) and the samples were allowed to thaw before SEC analysis. Results were difficult to analyze because there was no distinct dimer peak in the SEC chromatograms. Instead one could see a shoulder in front of the monomer peak more or less distinct as shown in FIG. 3.

2.2.3 Stress-Test of Human Monoclonal and Polyclonal Antibodies

Figure 4:
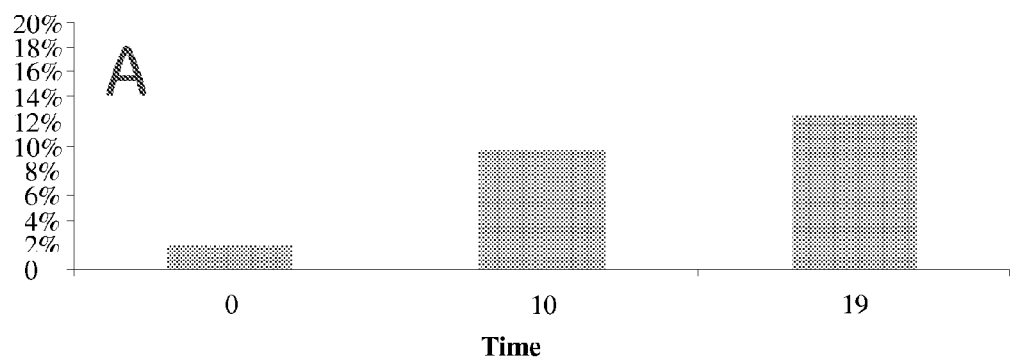
FIG. 4 shows the results from temperature stress test of human monoclonal antibody (B) and polyclonal GAM-MANORM® human antibody IgG (A) by freezing and thawing samples 5 times during 19 days. The samples at pH 7 are shown as they presented the largest effects. "0" sample represents non-frozen, freshly prepared start material.
Figure 4:
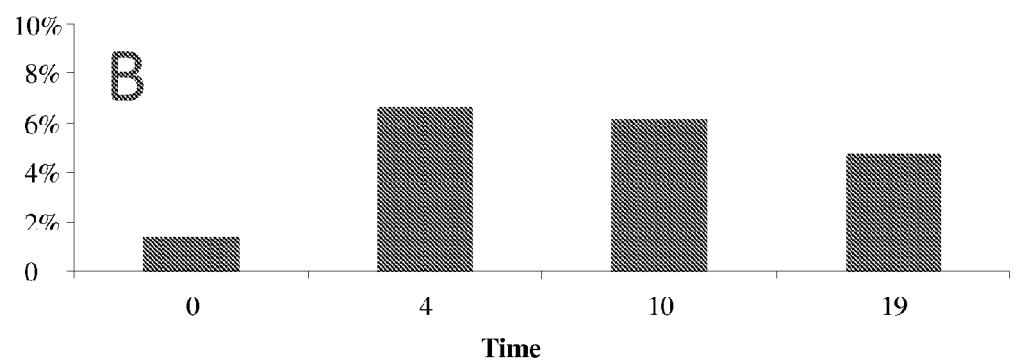

Three different buffers were prepared: 50 mM Na-Acetate, 150 mM NaCl, pH 5.0; 50 mM Na-Phosphate, 150 mM NaCl pH 7.0 and 50 mM Tris-HCl, 150 mM NaCl pH 9.0. Monomer fraction of purified human polyclonal IgG (1% dimer) and mab2 were applied to various PD-10 columns equilibrated with the three different buffers giving samples of the two antibodies in well defined buffers. Directly after buffer exchange, each sample was analyzed by SEC ("0" sample). 100 μl of each sample was pipetted into wells in a 96-well polypropylene plate. The samples in the 96-well plate were repetitively frozen and thawed (−20° C. to +20° C.) for a total of five freeze/thaw cycles. Results show that the treatment has an effect on the aggregate levels (FIG. 4, note that the dimer content in B is estimated due to absence of distinct dimer peaks.). The stress-tests has shown that aggregation is easily obtained in polyclonal or monoclonal antibody samples upon storage and during certain conditions there is an increase from 1% dimer to significant levels (e.g. 12-14%) in a short period of time.

2.3 Proof of Concept Experiments

It is generally known that the storage of proteins (e.g. antibodies) in solution leads to aggregation over time. By freezing the protein solutions in a carefully designed buffer environment at slow and controlled rates of freezing aggregation can be reduced, but the aggregate content will inevitably be higher after storage. Experiments were then performed using an alternative storage approach by using different gel media to bind or encapsulate the target proteins.

2.3.1 Storage of Human Polyclonal IgG with a Low Initial Dimer Content in Solution or on Gel Media The monomer fraction of human polyclonal IgG (1% dimer) was first concentrated to 121.5 AU (A280 nm) using VIVASPIN™ 6 ultrafiltration units and filtered with 0.2 μm syringe filters. Various experimental capture storage hydrogel media, and control (noncapture SEC) media (see Materials above) were dispensed into 96 well filter plates (MULTITRAP™ plates). The MULTITRAP™ protocol was followed using the concentrated monomer fraction of human polyclonal IgG as antibody sample. In parallel, antibody samples were mixed with the various buffers used for the different "gel media" for subsequent storage in solution at −20° C. 6.7 μl antibody solution was mixed with 13.3 μl of each buffer respectively.

Buffers used for samples and equilibration/washing of gel media were typical adsorption capture buffers for the different media used:

"pH 5 IEX"=20 mM Na-Acetate, 0.02% (w/v) Na-azide, pH 5.0

"pH 9 IEX"=20 mM Na-Glycine, 0.02% (w/v) Na-azide, pH 9.0

"PBS"=10 mM Na-Phosphate, 2.7 mM KCl, 0.14M NaCl, 0.02% (w/v) Na-azide, pH 7.4

"pH 5 HIC"=25 mM Na-Acetate, 0.5 mM EDTA, 0.75M $(NH_4)_2SO_4$, pH 5.0

The various chromatography gel media were stored in the 96-well MULTITRAP™ plate. The MULTITRAP™ plates were stored in the fridge for 4 weeks at 4-8° C. (the protocol incubation time), whereas the antibody samples in solution were stored at −20° C. for 4 weeks including 6 freeze/thaw cycles. All samples were run in triplicate except for three of the anion exchange gel media, CAPTO™ Q, Q SEPHAROSE™ FF and Q SEPHAROSE™ XL, that were run as single samples.

After incubation or storage for 4 weeks, either the non-bound antibodies (flow-through) were collected (gel filtration SEC media SEPHADEX™ G-50 and SUPERDEX™ 200) or the bound and then eluted antibodies (all media except gel filtration media). Elution and strip buffers used were:

elution buffer: "3.3×PBS"=30 mM Na-Phosphate, 8.1 mM KCl, 0.42 M NaCl, pH 7.4 (for those samples of which buffers used for samples and equilibration/washing of gel media were "pH 5 IEX" and "pH 9 IEX");

elution buffer: 0.1 M Na-Glycine pH 2.9 (for those samples of which buffers used for samples and equilibration/washing of gel media were "PBS);

elution and strip buffer: 20 mM Tris-HCl pH 7.5 (for those samples of which buffers used for samples and equilibration/washing of gel media were "pH 5 HIC");

strip buffer: 10 mM NaOH, 1M NaCl for those samples of which buffers used for samples and equilibration/washing of gel media were ("pH 5 IEX" and "pH 5 HIC");

strip buffer: 0.5M Acetic acid (for those samples of which buffers used for samples and equilibration/washing of gel media were "PBS" and "pH 9 IEX")

Elution was performed in two steps, first with elution buffers and secondly with strip buffers. The latter are typically in bioprocessing used to remove any residual protein not eluted by the elution buffers—and to prepare column for possible additional use. Both elution fractions for each sample were analyzed respectively. All samples, stored in solution, on SEC control media or on binding media, were analyzed by SEC. The results are shown in Tables 3A-3D.

TABLE 3A

Dimer content in eluted fractions from human polyclonal IgG stored on gel media at 4-8° C. or frozen in solution at −20° C. for 4 weeks in pH 5 "IEX" buffer (20 mM Na-Acetate, 0.02% (w/v) Na-azide, pH 5.0).

| Gel media | % dimer | replicate | comment |
|---|---|---|---|
| CAPTO ™ MMC | 1.72 | 1 | |
| CAPTO ™ MMC | 0.84 | 2 | |
| CAPTO ™ MMC | 0.75 | 3 | |
| CAPTO ™ S | 2.95 | 1 | |
| CAPTO ™ S | 2.53 | 2 | |
| CAPTO ™ S | 1.68 | 3 | |
| SP SEPHAROSE ™ FF | 2.68 | 1 | |
| SP SEPHAROSE ™ FF | 2.21 | 2 | |
| SP SEPHAROSE ™ FF | 2.58 | 3 | |
| SP XL | 2.44 | 1 | |
| SP XL | 1.84 | 2 | |
| SP XL | 1.72 | 3 | |

| Storage in solution (−20° C.) | % dimer | replicate | comment |
|---|---|---|---|
| pH 5 "IEX" | 3.41 | 1 | |
| pH 5 "IEX" | 3.23 | 2 | |
| pH 5 "IEX" | 3.92 | 3 | |

All samples stored on these gel media contained less antibody dimer content compared with storing the samples in solution at −20° C. The start material contained 1.0% dimer and two of the replicates using CAPTO™ MMC as storing gel media contained less dimer than this initial dimer content level.

TABLE 3B

Dimer content in eluted fractions from human polyclonal IgG stored on gel media at 4-8° C. or frozen in solution at −20° C. for 4 weeks in "PBS" buffer (10 mM Na-Phosphate, 2.7 mM KCl, 0.14M NaCl, 0.02% Na-azide, pH 7.4).

| Gel media | % dimer | replicate | comment |
|---|---|---|---|
| nProtein A SEPHAROSE ™ 4 FF | 0.31 | 1 | |
| nProtein A SEPHAROSE ™ 4 FF | 0.30 | 2 | <0.3, difficult to integrate peaks |
| nProtein A SEPHAROSE ™ 4 FF | 0.30 | 3 | <0.3, difficult to integrate peaks |
| MABSELECT ™ | 0.52 | 1 | |
| MABSELECT ™ | 0.50 | 2 | <0.5, difficult to integrate peaks |
| MABSELECT ™ | 0.50 | 3 | <0.5, difficult to integrate peaks |
| SUPERDEX ™ 200 | 4.25 | 1 | |
| SUPERDEX ™ 200 | 4.54 | 2 | |
| SUPERDEX ™ 200 | 4.14 | 3 | |
| SEPHADEX ™ G-50 | 4.93 | 1 | |
| SEPHADEX ™ G-50 | 5.18 | 2 | |
| SEPHADEX ™ G-50 | 4.94 | 3 | |

| Storage in solution (−20° C.) | % dimer | replicate | comment |
|---|---|---|---|
| PBS, pH 7.4 | 3.24 | 1 | |
| PBS, pH 7.4 | 3.27 | 2 | |
| PBS, pH 7.4 | 3.00 | 3 | |

Samples stored on the affinity gel media contained less antibody dimer compared with storing the samples in solution at −20° C. However, storage on noncapture SEC media resulted in higher levels of dimer. The start material contained 1.0% dimer and using nProtein A or MABSELECT™ as storing gel media resulted in less dimer content than the initial dimer content.

TABLE 3C

Dimer content in eluted fractions from human polyclonal IgG stored on gel media at 4-8° C. or frozen in solution at −20° C. for 4 weeks in "pH 5 HIC" buffer (25 mM Na-Acetate, 0.5 mM EDTA, 0.75M (NH$_4$)$_2$SO$_4$, pH 5.0).

| Gel media | % dimer | replicate | comment |
|---|---|---|---|
| Butyl SEPHAROSE ™ HP | 1.31 | 1 | |
| Butyl SEPHAROSE ™ HP | 1.05 | 2 | |
| Butyl SEPHAROSE ™ HP | 1.25 | 3 | |
| CAPTO ™ Phenyl high sub. | 0.10 | 1 | <0.1 |
| CAPTO ™ Phenyl high sub. | 0.10 | 2 | <0.1 |
| CAPTO ™ Phenyl high sub. | 0.00 | 3 | |
| pH HIC 2% | | | poor binding of sample at 0.75M AmSO |
| pH HIC 2% | | | poor binding of sample at 0.75M AmSO |
| pH HIC 2% | | | poor binding of sample at 0.75M AmSO |
| pH HIC 4% AMBN | | | poor binding of sample at 0.75M AmSO |
| pH HIC 4% AMBN | | | poor binding of sample at 0.75M AmSO |
| pH HIC 4% AMBN | | | poor binding of sample at 0.75M AmSO |
| SEPHAROSE ™ HP 16% AMBN | | | poor binding of sample at 0.75M AmSO |
| SEPHAROSE ™ HP 16% AMBN | | | poor binding of sample at 0.75M AmSO |
| SEPHAROSE ™ HP 16% AMBN | | | poor binding of sample at 0.75M AmSO |
| CAPTO ™ Phenyl low sub. | 1.15 | 1 | |
| CAPTO ™ Phenyl low sub. | 0.87 | 2 | |
| CAPTO ™ Phenyl low sub. | 1.26 | 3 | |
| SEPHAROSE ™ HP 16% AMBN | | | poor binding of sample at 0.75M AmSO |
| SEPHAROSE ™ HP 16% AMBN | | | poor binding of sample at 0.75M AmSO |
| SEPHAROSE ™ HP 16% AMBN | | | poor binding of sample at 0.75M AmSO |

| Storage in solution (−20° C.) | % dimer | replicate | comment |
|---|---|---|---|
| pH 5 "HIC" | 1.55 | 1 | |
| pH 5 "HIC" | 1.74 | 2 | |
| pH 5 "HIC" | 1.69 | 3 | |

The overall recoveries from the HIC gel media were poor, probably due to poor binding of the antibodies due to using too low a conductivity (salt concentration) in the adsorption buffer. To promote binding to the HIC gel media a higher concentration of (NH$_4$)$_2$SO$_4$ was needed. The results that were obtained showed that binding to the gel media gives less dimer during storage compared with storage in solution and for CAPTO™ Phenyl high substitution (higher ligand concentration) media the dimer content was less than 1.0% (level in the start material).

TABLE 3D

Dimer content in eluted fractions from human polyclonal IgG stored on gel media at 4-8° C. or frozen in solution at −20° C. for 4 weeks in "pH 9 IEX" buffer (20 mM Na-Glycine, 0.02% (w/v) Na-azide, pH 9.0).

| Gel media | % dimer | replicate | comment |
|---|---|---|---|
| CAPTO ™ Adhere | 0.69 | 1 | |
| CAPTO ™ Adhere | 0.95 | 2 | |
| CAPTO ™ Adhere | 0.75 | 3 | |
| CAPTO ™ Q | 2.27 | 1 | |
| CAPTO ™ Q | | | no sample |
| CAPTO ™ Q | | | no sample |
| Q SEPHAROSE ™ FF | 3.84 | 1 | |
| Q SEPHAROSE ™ FF | | | no sample |

TABLE 3D-continued

Dimer content in eluted fractions from human polyclonal IgG stored on gel media at 4-8° C. or frozen in solution at −20° C. for 4 weeks in "pH 9 IEX" buffer (20 mM Na-Glycine, 0.02% (w/v) Na-azide, pH 9.0).

| Q SEPHAROSE ™ FF | | | no sample |
|---|---|---|---|
| Q XL | 3.31 | 1 | |
| Q XL | | | no sample |
| Q XL | | | no sample |

| Storage in solution (−20° C.) | % dimer | replicate | comment |
|---|---|---|---|
| pH 9 "IEX | 3.39 | 1 | |
| pH 9 "IEX | 3.35 | 2 | |
| pH 9 "IEX | 3.58 | 3 | |

Figure 5:
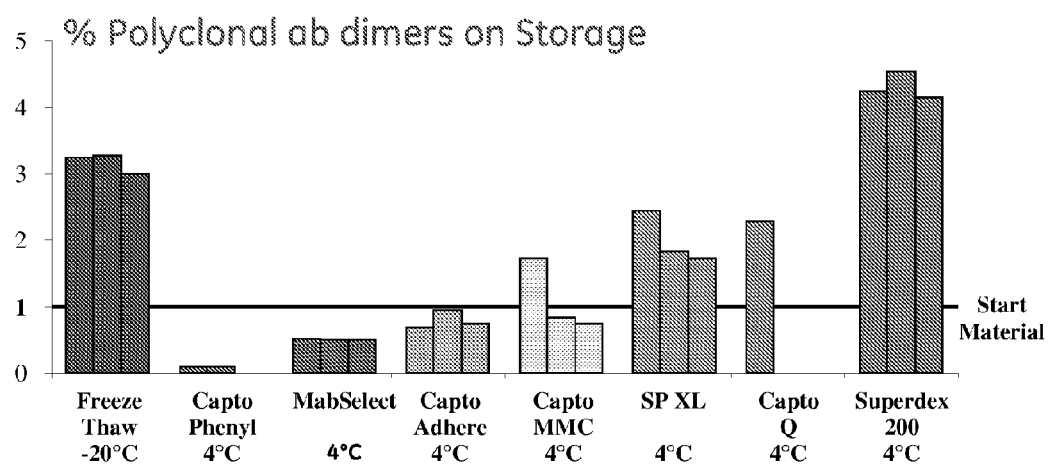
FIG. 5 shows the dimer content after storage of polyclonal antibody in pH 7.4 phosphate buffered saline solution after repetitive freeze/thawing 6 times and storage on various gel media. Storage time was 4 weeks.

Samples stored on CAPTO™ Adhere gel media contained less antibody dimer content compared with storing the samples in solution at −20° C. The dimer content was less than 1.0% as found in the start material. Storage on the other gel media resulted in about the same levels of dimeric proteins as storage in solution. Selected results are summarized in FIG. 5.

2.3.2 Storage of Human Polyclonal IgG with a High Initial Dimer Content in Solution or on Gel Media Polyclonal human IgG (GAMMANORM® 165 mg/ml) was diluted to 30 mg/ml with following equilibration/wash buffers:
  20 mM Na-Acetate, 0.02% (w/v) Na-azide, pH 5.0
  20 mM Na-Glycine, 0.02% (w/v) Na-azide, pH 9.0
  10 mM Na-Phosphate, 2.7 mM KCl, 0.14M NaCl, 0.02% (w/v) Na-azide, pH 7.4
  50 mM Na-Acetate, 1 mM EDTA, 1.5M $(NH_4)_2SO_4$, pH 5.0

Some protein was precipitated upon mixing the antibody solution with the fourth buffer solution containing 1.5M $(NH_4)_2SO_4$. The absorbance of these start materials were measured (on clarified solutions):

| Sample buffer | A 280 cm$^{-1}$ |
|---|---|
| 20 mM Na Acetate, 0.02% (w/v) Na azide, pH 5.0 | 40.6 |
| 20 mM Na Glycine, 0.02% (w/v) Na azide, pH 9.0 | 40.5 |
| 10 mM Na Phosphate, 2.7 mM KCl, 0.14M NaCl, 0.02% (w/v) Na azide, pH 7.4 | 40.8 |
| 50 mM Na Acetate, 1 mM EDTA, 1.5M $(NH_4)_2SO_4$, pH 5.0 | 28.5 |

SPINTRAP™ columns were filled with 40 µl of following gel media (i.e. 200 µl 20% gel slurry) and were equilibrated according to the SPINTRAP™ protocol:
  CAPTO™ MMC mixed mode media, 20 mM Na-Acetate, 0.02% (w/v) Na-azide, pH 5.0
  CAPTO™ S cation exchange media, 20 mM Na-Acetate, 0.02% (w/v) Na-azide, pH 5.0
  CAPTO™ Adhere mixed mode media, 20 mM Na-Glycine, 0.02% (w/v) Na-azide, pH 9.0
  CAPTO™ Q anion exchange media, 20 mM Na-Glycine, 0.02% (w/v) Na-azide, pH 9.0
  MABSELECT™, affinity media, 10 mM Na-Phosphate, 2.7 mM KCl, 0.14M NaCl, 0.02% (w/v) Na-azide, pH 7.4
  SEPHADEX™ G-50, control SEC media, 10 mM Na-Phosphate, 2.7 mM KCl, 0.14M NaCl, 0.02% (w/v) Na-azide, pH 7.4
  CAPTO™ Phe hs, phenyl ligand containing HIC media, 50 mM Na-Acetate, 1 mM EDTA, 1.5M $(NH_4)_2SO_4$, pH 5.0
  pH HIC 6%, pH responsive polymer based HIC media, 50 mM Na-Acetate, 1 mM EDTA, 1.5M $(NH_4)_2SO_4$, pH 5.0
  pH HIC 16%, pH responsive polymer based HIC media, 50 mM Na-Acetate, 1 mM EDTA, 1.5M $(NH_4)_2SO_4$, pH 5.0

After equilibration, 40 µl of sample was added to each column (matching buffers). Three SPINTRAP™ columns of each gel media containing bound antibodies were stored at room temperature (+20° C.), in fridge (+4-8° C.) and in the freezer (−20° C.) respectively. In parallel, aliquots of antibodies in solution containing the various buffers were also stored at the same temperatures as the SPINTRAP™ columns.

60 µl of matching buffer was added to all SPINTRAP™ columns after an incubation time of 24-26 days. The flow-through (non-binding fraction) was collected and the absorbance (A280 nm) was measured.

The various gel media was washed, then eluted with 400 µl of following elution buffers:
  CAPTO™ MMC, 20 mM Na-Phosphate, 1M NaCl, pH 7.0
  CAPTO™ S, 20 mM Na-Phosphate, 1M NaCl, pH 7.0
  CAPTO™ Adhere, 0.5M Acetic acid
  CAPTO™ Q, 20 mM Na-Phosphate, 1M NaCl, pH 7.0
  MABSELECT™, 0.5M Acetic acid
  SEPHADEX™ G-50, not eluted, flow-through fraction collected
  CAPTO™ Phe hs, 20 mM Na-Phosphate, 1M NaCl, pH 7.0
  pH HIC 6%, 20 mM Na-Phosphate, 1M NaCl, pH 7.0
  pH HIC 16%, 20 mM Na-Phosphate, 1M NaCl, pH 7.0

The absorbance (A280 nm) was measured on the eluted fractions. All samples from storage in solution and flow-through/elution fractions from the various gel media were analyzed by SEC. The antibody recovery and the dimer content are summarized in Table's 4A-4D.

TABLE 4A

Antibody recovery and dimer content in eluted fractions after storage of human polyclonal IgG on gel media or in solution. Buffer for storage: 20 mM Na-Acetate, 0.02% (w/v) Na-azide, pH 5.0. Initial dimer content directly after dilution was 16.9%.

| Storage on gel media | Temp. ° C. | % dimer after 3.5 weeks | Total protein recovery % | Monomer IgG recovery % |
|---|---|---|---|---|
| CAPTO ™ MMC | 20 | 8.0 | 24 | 27 |
| 20 mM acetate pH 5.0 | 5 | 11.1 | 71 | 82 |
|  | −20 | 10.7 | 76 | 87 |
| CAPTO ™ S | 20 | 6.4 | 87 | 98 |
| 20 mM acetate pH 5.0 | 5 | 8.5 | 93 | 108 |
|  | −20 | 8.3 | 88 | 101 |

| In solution storage | Temp. ° C. | % dimer after 3.5 weeks | Total protein recovery % | Monomer IgG recovery % |
|---|---|---|---|---|
| 20 mM acetate pH 5.0 | 20 | 11.6 | | |
|  | 5 | 13.8 | | |
|  | −20 | 13.0 | | |

Storage on CAPTO ™ S results in much reduced dimer content and the antibody recovery is high. CAPTO ™ MMC gives slightly lower dimer content after storage compared with storage in solution with good recoveries at lower temperatures.

TABLE 4B

Antibody recovery and dimer content in eluted fractions after storage of human polyclonal IgG on gel media or in solution. Buffer for storage: 20 mM Na-Glycine, 0.02% (w/v) Na-azide, pH 9.0. Initial dimer content directly after dilution was 24.4%.

| Storage on gel media | Temperature °C. | % dimer after 3.5 weeks | Total protein recovery % | Monomer IgG recovery % |
|---|---|---|---|---|
| CAPTO ™ Adhere | 20 | 4.0 | 88 | 111 |
| 20 mM glycine pH 9 | 5 | 1.5 | 93 | 122 |
|  | −20 | 2.0 | 93 | 109 |
| CAPTO ™ Q | 20 | 7.4 | 72 | 91 |
| 20 mM glycine pH 9 | 5 | 9.0 | 57 | 74 |
|  | −20 | 7.5 | 66 | 77 |

| In solution storage | Temperature °C. | % dimer after 3.5 weeks | Total protein recovery % | Monomer IgG recovery % |
|---|---|---|---|---|
| 20 mM glycine pH 9 | 20 | 20.9 | | |
|  | 5 | 23.5 | | |
|  | −20 | 14.5 | | |

Storage on CAPTO ™ Adhere gives much improved results compared with storage in solution. The recoveries are very high with possible conversion of dimers into monomers as evidenced by the higher than 100% recovery of monomer IgG. Results from storage on CAPTO ™ Q show less dimer content compared with storage in solution, but the recoveries were less than 80%.

TABLE 4C

Human polyclonal IgG antibody recovery and dimer content in eluted fractions after storage. Buffer for storage: 10 mM Na-Phosphate, 2.7 mM KCl, 0.14 M NaCl, 0.02% (w/v) Na-azide, pH 7.4. Initial dimer content directly after dilution was 24.6%.

| Storage on gel media | Temperature °C. | % dimer after 3.5 weeks | Total protein recovery % | Monomer IgG recovery % |
|---|---|---|---|---|
| MABSELECT ™ | 20 | 1.7 | 88 | 108 |
| PBS, pH 7.4 | 5 | 2.2 | 89 | 115 |
|  | −20 | 2.1 | 90 | 116 |
| SEPHADEX ™ G-50 | 20 | 14.4 | 98 | 120 |
| PBS, pH 7.4 | 5 | 17.0 | 73 | 94 |
|  | −20 | 14.4 | 97 | 125 |

| In solution storage | Temperature °C. | % dimer after 3.5 weeks | Total protein recovery % | Monomer IgG recovery % |
|---|---|---|---|---|
| PBS, pH 7.4 | 20 | 18.3 | | |
|  | 5 | 22.4 | | |
|  | −20 | 22.3 | | |

Storage on MABSELECT ™ gives much improved results compared with storage in solution. The recoveries are very high with possible conversion of dimers into monomers evidenced by the higher than 100% recovery of monomer IgG. Results from storage on SEPHADEX ™ G-50 show slightly less dimer content compared with storage in solution but have the highest protein recovery of all gel media perhaps due to the non-binding properties.

TABLE 4D

Human polyclonal IgG antibody recovery and dimer content in eluted fractions after storage. Buffer for storage: 50 mM Na-Acetate, 1 mM EDTA, 1.5M (NH$_4$)$_2$SO$_4$, pH 5.0. Initial dimer content directly after dilution was not measured due to precipitation.

| Storage on gel media | Temperature °C. | % dimer after 3.5 weeks | Total protein recovery % | Monomer IgG recovery % |
|---|---|---|---|---|
| CAPTO ™ Phe hs | 20 | 6.5 | 31 | |
|  | 5 | 5.7 | 49 | |
|  | −20 | 7.7 | 57 | |
| pH HIC 16% | 20 | 5.9 | 70 | |
|  | 5 | 6.9 | 79 | |
|  | −20 | 9.0 | 68 | |

TABLE 4D-continued

Human polyclonal IgG antibody recovery and dimer content in eluted fractions after storage. Buffer for storage: 50 mM Na-Acetate, 1 mM EDTA, 1.5M (NH$_4$)$_2$SO$_4$, pH 5.0. Initial dimer content directly after dilution was not measured due to precipitation.

| Storage on gel media | Temperature °C. | % dimer after 3.5 weeks | Total protein recovery % | Monomer IgG recovery % |
|---|---|---|---|---|
| pH HIC 6% | 20 | 5.7 | 68 | |
|  | 5 | 7.4 | 80 | |
|  | −20 | 8.2 | 82 | |

For HIC gel media, there was no starting material for comparison due to target precipitation. The absorbance (A280 nm) of the start material was 28.5 AU compared with over 40 AU for the other start materials. The protein recovery after clarification was good for pH HIC 6% and pH HIC 16% gel media. Compared with other gel media, the dimer content after storage was in the low range, showing a positive effect on aggregation stabilization or reduction.

Figure 6:
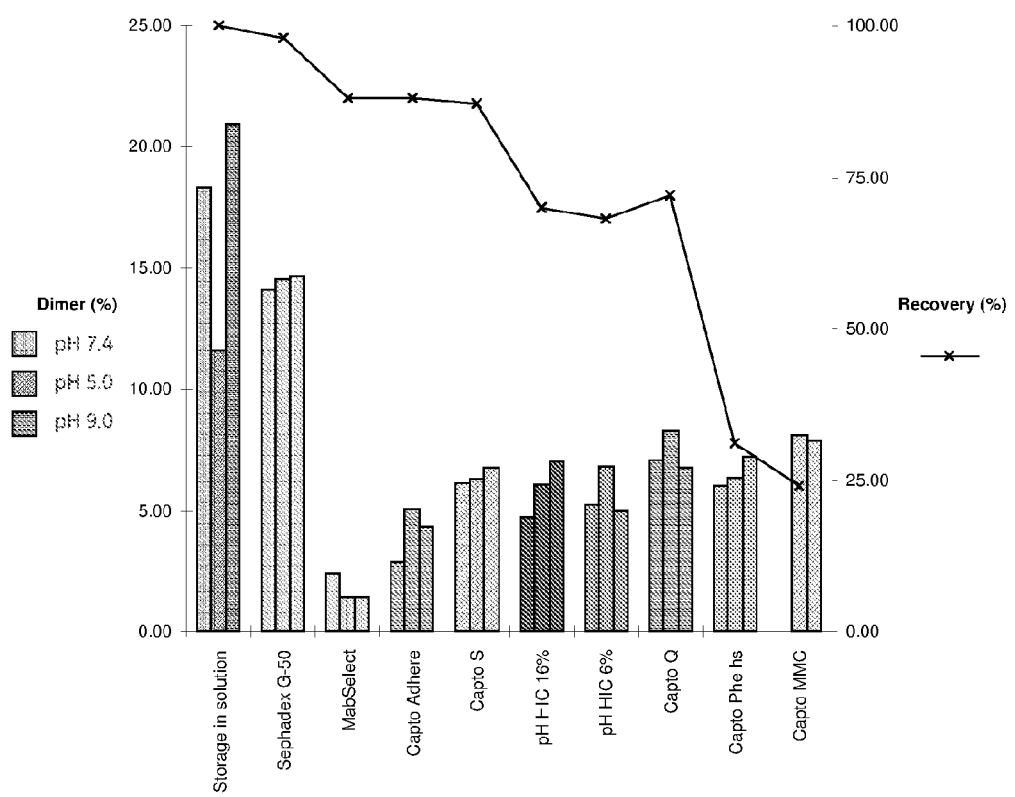
FIG. 6A is a bar graph showing dimer content after storage of polyclonal antibodies in solution or on various gel media for 3.5 weeks at +20° C. Storage in solution is represented by three different buffers (PBS: 0.15M NaCl, 0.01M NaPhosphate pH 7.4; 20 mM Na-Acetate pH 5.0, and 20 mM Na-Glycine pH 9.0 respectively). The average total protein recovery is indicated by the line graph.
FIG. 6B is a bar graph showing dimer content after storage of polyclonal antibodies in solution or on various gel media for 3.5 weeks at +4-+8° C. Storage in solution is represented by three different buffers (PBS pH 7.4, 20 mM Na-Acetate pH 5.0, and 20 mM Na-Glycine pH 9.0 respectively). The average total protein recovery is indicated by the line graph.
FIG. 6C is a bar graph showing dimer content after storage of polyclonal antibodies in solution or on various gel media for 3.5 weeks at −20° C. Storage in solution (frozen) is represented by three different buffers (PBS pH 7.4, 20 mM Na-Acetate pH 5.0, and 20 mM Na-Glycine pH 9.0 respectively). The average total protein recovery is indicated by the line graph.
Figure 6:
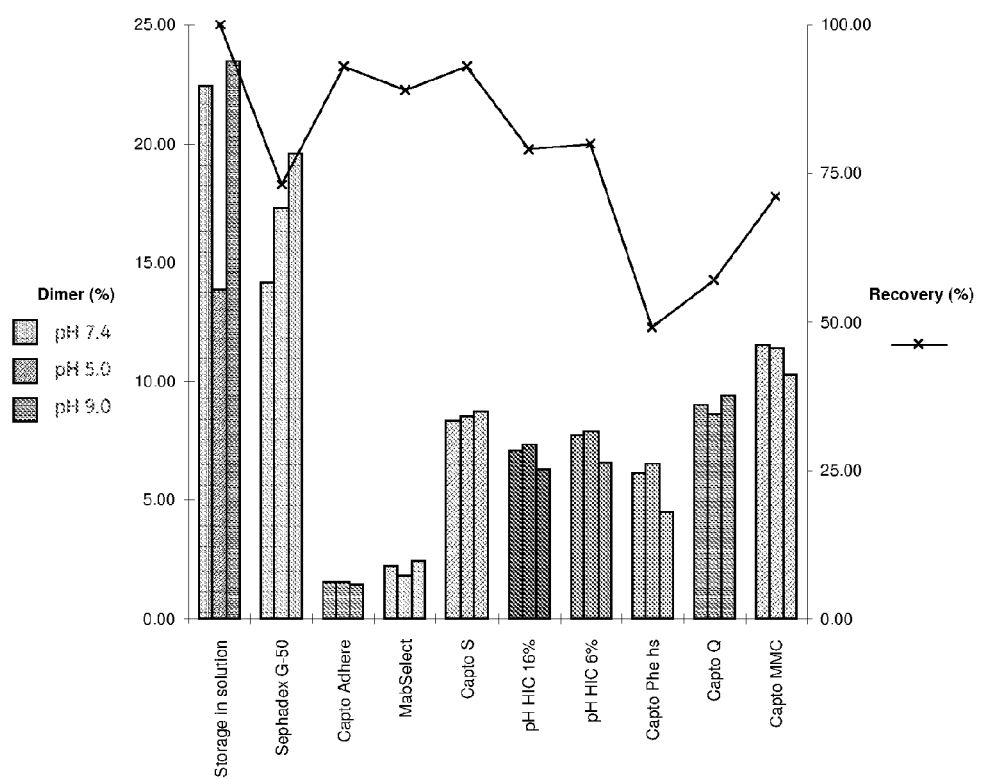
Figure 6:
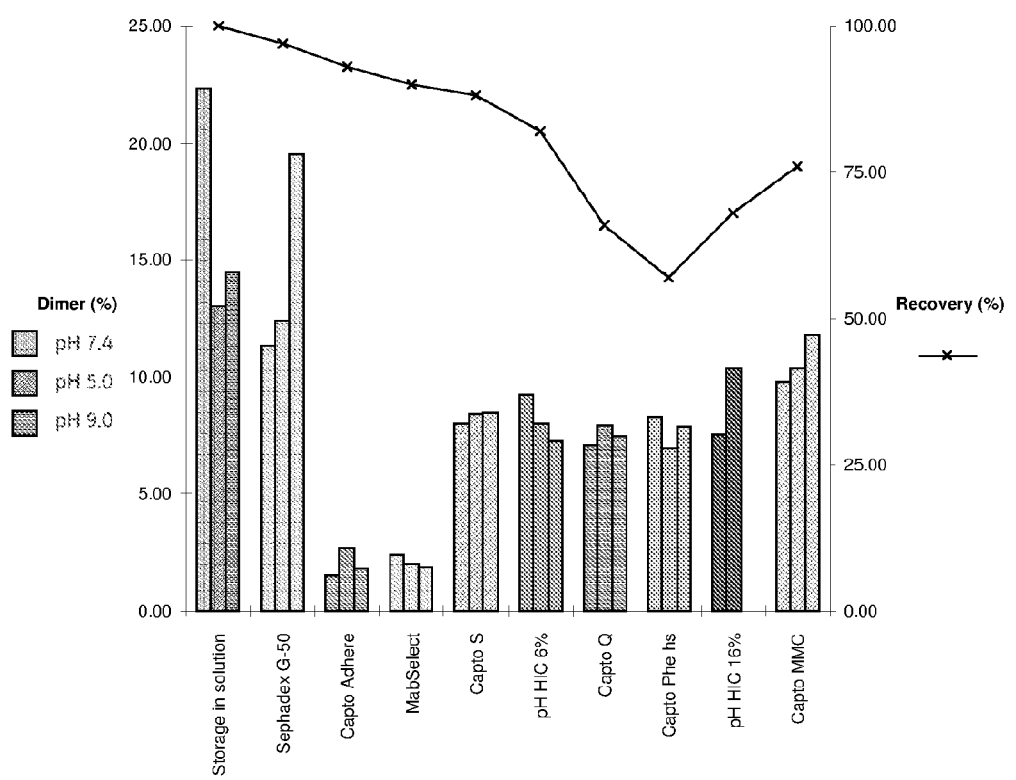

The results for all storage conditions are shown as graphs in FIGS. 6A-C. Storage on CAPTO™ Adhere or on MABSELECT™ shows very low levels of dimers or aggregates with high recoveries of monomer IgG after storage, reflecting apparent ability of the media to reduce dimer levels during storage.

The initial dimer content directly after dilution of GAMMANORM® (165 mg/ml) was between 16.9-24.6% depending on buffer used. After storage for 3.5 weeks at different temperatures, the dimer content was slightly lower in the various solutions.

The buffer composition, pH, salt content and type seem to affect the equilibrium faster and to a higher degree than compared with the protein concentration. Storage of GAMMANORM® in a low salt buffer at pH 5.0 results in much lower dimer content compared with storage at pH 7.4 or pH 9.0, both directly after dilution and after storage for 3.5 weeks.

The effect of temperature is less obvious.

The best storage condition for GAMMANORM® in solution seems to be storage in 20 mM Na-Acetate, 0.02% Na-azide pH 5.0 at +20° C. according to these experiments.

However, the most pronounced effect on dimer content was observed when storing antibodies on binding media. Especially on CAPTO™ Adhere and MABSELECT™, although storage on these gel media was done at pH 9.0 and pH 7.4 respectively. The effect was so great, that when calculating the recovery of monomeric IgG, the result was higher than 100% for samples stored on CAPTO™ Adhere and MABSELECT™. The total protein recovery was never higher than 98% though (SEPHADEX™ G-50, non-binding media).

Thus, storing on binding media may have several benefits including:
1. Stabilization of IgG against aggregation (slow down kinetics)
2. Removal of IgG dimer (polishing)
3. Promote monomer formation (reversal of monomer/dimer equilibrium)

Storing a start material with low initial dimer content on gel media would benefit from stabilization and polishing. Starting from high initial dimer content would also benefit from reducing the amount of dimers and increase the percent of monomers.

Results obtained from non-binding media show no or little reduction of dimer content. In the first experiment starting with low initial dimer content, the storage on non-binding gel media (SUPERDEX™ 200 and SEPHADEX™ G-50) resulted in slightly more dimers compared with storing in solution. Starting with high initial dimer content, the storage on SEPHADEX™ G-50 resulted in slightly less dimers compared with storage in solution. The overall dimer content was however always higher compared with storing on any capture gel media.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A method for reducing aggregates in a target substance during a wet storage, the method comprising:
   (a) providing a sample containing said target substance in a suitable buffer;
   (b) combining said sample with a capture media to effect reversible binding of the target substance to the capture media with the target substance in a hydrated state;
   (c) storing said capture media with the target substance reversibly bound thereto in a hydrated state, at between about −20 and 20° C., for at least an amount of time which allows a significant amount of aggregates of the target substance to separate into monomeric form; and
   (d) recovering said target substance from said capture media,
   wherein the target substance recovered contains a significantly less amount of aggregated form of the target substance compared to the target substance before the storage, is not denatured throughout the method, and maintains a desired activity, and
   wherein the capture media is a protein A based affinity media or a multimodal strong anion exchange media that comprises a ligand comprising N-Benzyl-N-methyl ethanol amine.

2. The method of claim 1, wherein the target substance is monoclonal or polyclonal antibody.

3. The method of claim 1, wherein the target substance at the combining step is at a concentration of about 1 to 300 g/L (mg/mL) volume.

4. The method of claim 1, wherein said sample is selected from the group of cell culture supernatant, cell culture lysate, bacterial culture supernatant, bacterial culture lysate, blood or other body fluids.

5. The method of claim 1, wherein combining step is performed in a container selected from column, bag, tank, cassette, or other housing and the container is capable of supporting the binding between the target substance and the capture media, as well as the storage step.

6. The method of claim 1, wherein the capture media with the target substance reversibly bound thereto is stored for less than 2 weeks.

7. The method of claim 1, wherein the capture media with the target substance reversibly bound thereto is stored for about 2-4 weeks.

8. The method of claim 1, wherein the recovering step includes eluting the target substance from the capture media and collecting the eluent containing the target substance.

9. The method of claim 1, wherein the capture media comprises highly cross-linked agarose.

10. The method of claim 1, wherein the recovery rate is at least 75%.

11. The method of claim 1, wherein the recovery rate is at least 50%.

12. The method of claim 1, wherein the combining step is performed in a container selected from column, bag, tank, cassette, or other housing and the container is capable of supporting the binding between the target substance and the capture media as well as the storage step.

13. The method of claim 12, wherein said container is transportable and/or can withstand freezing.

14. The method of claim 1, wherein the capture media with the target substance reversibly bound thereto is stored at about −20° C., 4° C., or 20° C.

15. The method of claim 1, wherein the capture media with the target substance reversibly bound thereto may be stored at temperatures up to 40° C.

16. The method of claim 1, wherein the capture media with the target substance reversibly bound thereto is stored for more than 4 weeks.

17. A method for reducing aggregates in a target substance during a wet storage, the method comprising:
   (a) providing a sample containing said target substance in a suitable buffer;
   (b) combining said sample with a capture media to effect reversible binding of the target substance to the capture media with the target substance in a hydrated state;
   (c) storing said capture media with the target substance reversibly bound thereto in a hydrated state, at between about −20 and 20° C., for at least a day; and
   (d) recovering said target substance from said capture media,
   wherein the target substance recovered contains a significantly less amount of aggregated form of the target substance compared to the target substance before the storage, is not denatured throughout the method, and maintains a desired activity, and
   wherein the capture media is affinity media.

18. The method of claim 17, wherein the target substance is monoclonal or polyclonal antibody.

19. The method of claim 17, wherein the target substance at the combining step is at a concentration of about 1 to 300 g/L (mg/mL) volume.

20. The method of claim 17, wherein said sample is selected from the group of cell culture supernatant, cell culture lysate, bacterial culture supernatant, bacterial culture lysate, blood or other body fluids.

21. The method of claim 17, wherein combining step is performed in a container selected from column, bag, tank, cassette, or other housing and the container is capable of supporting the binding between the target substance and the capture media, as well as the storage step.

22. The method of claim 17, wherein the capture media with the target substance reversibly bound thereto is stored for less than 2 weeks.

23. The method of claim 17, wherein the capture media with the target substance reversibly bound thereto is stored for more than 2 weeks.

24. The method of claim 17, wherein the recovering step includes eluting the target substance from the capture media and collecting the eluent containing the target substance.

25. The method of claim 17, wherein the capture media comprises highly cross-linked agarose.

26. The method of claim 17, wherein the recovery rate is at least 75%.

27. The method of claim 17, wherein the recovery rate is at least 50%.

28. The method of claim 17, wherein the target substance is selected from proteins, peptides, oligopeptides, oligonucleotides, RNA, DNA, protein vaccine, virus vaccine, and other sensitive therapeutic substance.

29. A method for reducing aggregates in a target substance during a wet storage, the method comprising:
 (a) providing a sample containing said target substance in a suitable buffer;
 (b) combining said sample with a capture media to effect reversible binding of the target substance to the capture media with the target substance in a hydrated state;
 (c) storing said capture media with the target substance reversibly bound thereto in a hydrated state, at between about −20 and 20° C., for at least a day; and
 (d) recovering said target substance from said capture media,
 wherein the target substance recovered contains a significantly less amount of aggregated form of the target substance compared to the target substance stored in solution, is not denatured throughout the method, and maintains a desired activity.

30. The method of claim 29, wherein target substance is bound to the capture media through ion-exchange interaction, cation-pi interaction, pi-pi interaction, hydrogen bonding interaction, metal ion affinity, hydrophobic interaction, boronate glycomolecule affinity, or combinations of such interactions via mixed mode, hydroxyapatite, blue dye ligand, or affinity interactions including lectin and protein ligand based affinities.

* * * * *